(12) United States Patent　　(10) Patent No.: US 10,168,302 B2
Lennox et al.　　(45) Date of Patent: Jan. 1, 2019

(54) SIGNAL PROCESSING SYSTEM AND METHODS

(71) Applicant: The University of Manchester, Greater Manchester (GB)

(72) Inventors: Barry Lennox, Cheshire (GB); Keir Groves, Wiltshire (GB)

(73) Assignee: The University of Manchester, Manchester (GB)

( * ) Notice: Subject to any disclaimer, the term of this patent is extended or adjusted under 35 U.S.C. 154(b) by 278 days.

(21) Appl. No.: 15/028,661

(22) PCT Filed: Oct. 13, 2014

(86) PCT No.: PCT/GB2014/053070
§ 371 (c)(1),
(2) Date: Apr. 11, 2016

(87) PCT Pub. No.: WO2015/052542
PCT Pub. Date: Apr. 16, 2015

(65) Prior Publication Data
US 2016/0258906 A1　　Sep. 8, 2016

(30) Foreign Application Priority Data
Oct. 11, 2013　(GB) .................................. 1318067.4

(51) Int. Cl.
*G01M 3/24*　　(2006.01)
*G01N 29/09*　　(2006.01)
*G01N 29/46*　　(2006.01)
*G01M 3/02*　　(2006.01)

(52) U.S. Cl.
CPC .............. *G01N 29/09* (2013.01); *G01M 3/02* (2013.01); *G01M 3/243* (2013.01); *G01N 29/46* (2013.01); *G01N 2291/0289* (2013.01); *G01N 2291/2636* (2013.01)

(58) Field of Classification Search
CPC ........ G01N 29/09; G01N 29/46; G01M 3/243
See application file for complete search history.

(56) References Cited

U.S. PATENT DOCUMENTS

| 3,346,067 | A |  | 10/1967 | Schroeder |
| 4,732,039 | A |  | 3/1988 | Syed |
| 9,261,484 | B1 | * | 2/2016 | Juan ..................... G01N 29/028 |
| 9,500,554 | B2 | * | 11/2016 | Kulkarni ............... G01M 3/002 |

(Continued)

FOREIGN PATENT DOCUMENTS

| CA | 2119872 A1 | 5/1994 |
| GB | 2140919 A | 12/1984 |
| JP | H01-245121 A | 9/1989 |

(Continued)

OTHER PUBLICATIONS

Faital Pro Product Datasheet: "HF104 Compression Driver", Faital S.p. A., first considered/reviewed on Jun. 25, 2013, 2 pages.

(Continued)

*Primary Examiner* — Benjamin Sandvik
(74) *Attorney, Agent, or Firm* — Wilmer Cutler Pickering Hale and Dorr LLP

(57) ABSTRACT

Embodiments relate to a signal processing system and method in particular for determining the location of a feature within a hollow body using deconvolution of measured acoustic waves.

33 Claims, 11 Drawing Sheets

(56) References Cited

U.S. PATENT DOCUMENTS

Figure 1:
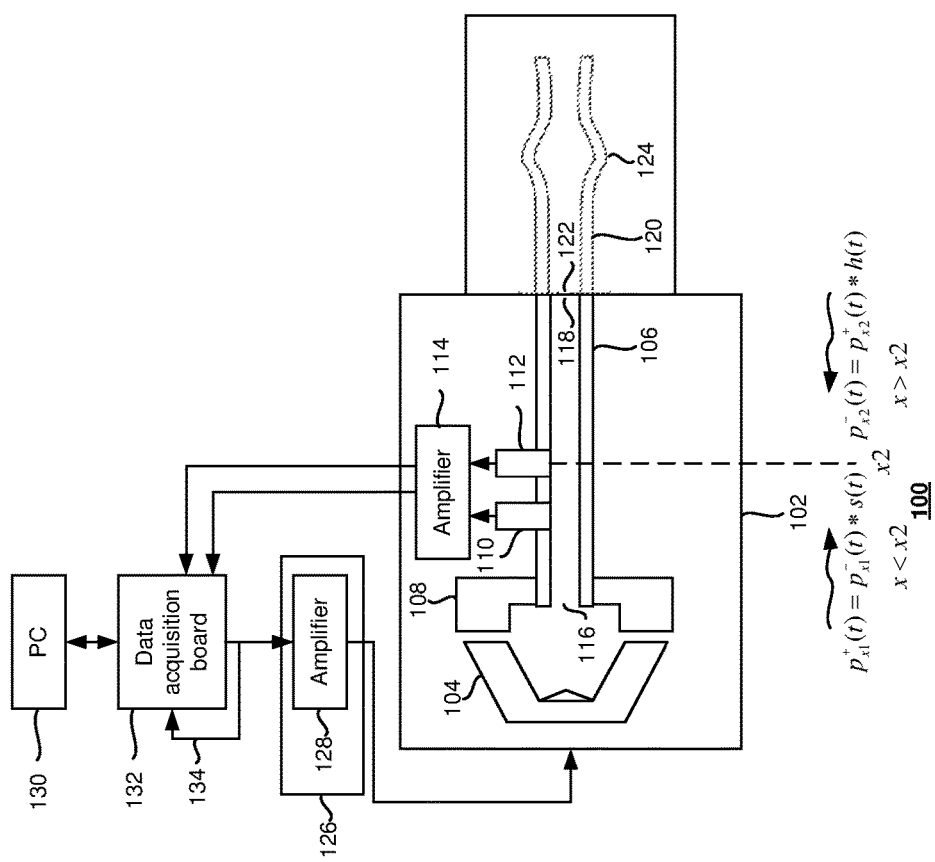

2002/0134144 A1* 9/2002 Gysling ............... G01H 5/00
                                             73/61.79
2005/0210960 A1* 9/2005 Shamout ............ G01M 3/243
                                             73/40.5 A

FOREIGN PATENT DOCUMENTS

| JP | H09-33239 A | 2/1997 |
| JP | 2004-061361 A | 2/2004 |
| JP | 2004-085515 A | 3/2004 |
| JP | 2005-134207 A | 5/2005 |
| WO | WO-0237468 A1 | 5/2002 |
| WO | WO-03/048713 A1 | 6/2003 |
| WO | WO-2007013068 A2 | 2/2007 |

OTHER PUBLICATIONS

Louis et al., "Airway Area by Acoustic Reflection: The Two-Microphone Method", Journal of Biomechanical Engineering, Transactions of the ASME, vol. 115, pp. 278-285, Aug. 1993.
Sennheiser Product Datasheet, "KE 4-211-2: Components—Microphone Capsule", first considered/reviewed on Jun. 25, 2013, 2 pages.
Forbes et al., "Singular System Methods in Acoustic Pulse Reflectometry," Acta Acustica United With Acustica, vol. 89, No. 5, pp. 743-753, Sep. 1, 2003.
International Preliminary Report on Patentability dated Apr. 21, 2016, in the international application PCT/GB2014/053070, 9 pages.
International Search Report and Written Opinion dated Jan. 26, 2015, in the international application PCT/GB2014/053070, 11 pages.

* cited by examiner

SIGNAL PROCESSING SYSTEM AND METHODS

CROSS-REFERENCE TO RELATED APPLICATIONS

This application is a 35 U.S.C. 371 National Stage of International Patent Application No. PCT/GB2014/053070, entitled "Signal Processing System and Methods", filed Oct. 13, 2014, which designated the U.S. and which claims priority to and the benefit of GB 1318067.4, filed Oct. 11, 2013.

Embodiments relate to signal processing systems and methods and, in particular, to signal processing systems and methods for investigating an object.

An existing inspection apparatus and method for pipe inspection uses an acoustic pulse reflectometry technique disadvantageously requiring both complex calibration and exact knowledge of the excitation pulse in determining an object's impulse response as can be appreciated from WO2007/013068.

It is an object of embodiments at least to mitigate one or more problems of the prior art.

Accordingly, embodiments provide an inspection method to identify an acoustic impulse response associated with a hollow body; the method comprising the steps of resolving a plurality of measured resultant forwards and backwards pressure waveforms, $p_{x1}(t)$, $p_{x2}(t)$, . . . , $p_{xn}(t)$ and $p_{x2}(t)$, associated with the hollow body into one or more than one function of time shifted versions of the forwards and backwards pressure waveforms; the one or more than one function being a function of the plurality of measured resultant pressure waveforms measured at respective positions; the plurality of measured resultant forwards and backwards pressure waveforms representing measurements by a plurality of acoustic detection devices positioned at the respective positions of a launch body for exciting the hollow body using an excitation waveform;

deriving the acoustic impulse response, $h(t)$, or transfer function of the hollow body from said one or more than one function of time shifted versions of the forwards and backwards pressure waveforms.

Advantageously, knowledge of, for example, the emitted wave is not required to characterise an object, such as, a hollow body, like, for example, a pipe, a pipe network or other object.

Embodiments can distinguish between various types of anomaly such as, for example, holes and other defects such as, for example, pits, corrosion, sludge, sediment, cracks, fractures, accumulations. The distinguishing is undertaken on the basis of the anomalies having respective characteristic acoustic impedances and/or respective acoustic impulse responses. Furthermore, other anomalies or features of interest comprise T-pieces, flanges, weld joints, sensors, devices, valves, bends, deformations, peeling coatings, inner lumen linings, absence of linings and the like. Again, such features have characteristic acoustic impedances and/or respective acoustic impulse responses and such characteristic impedances and/or acoustic impulse responses are associated with the pipe.

Figure 2:
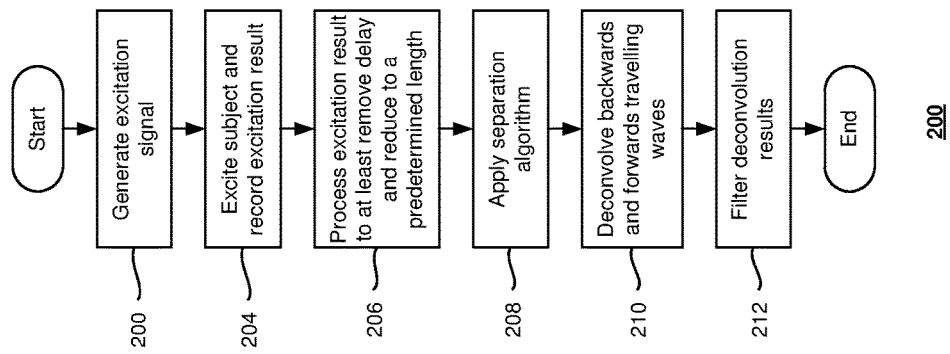
Figure 3:
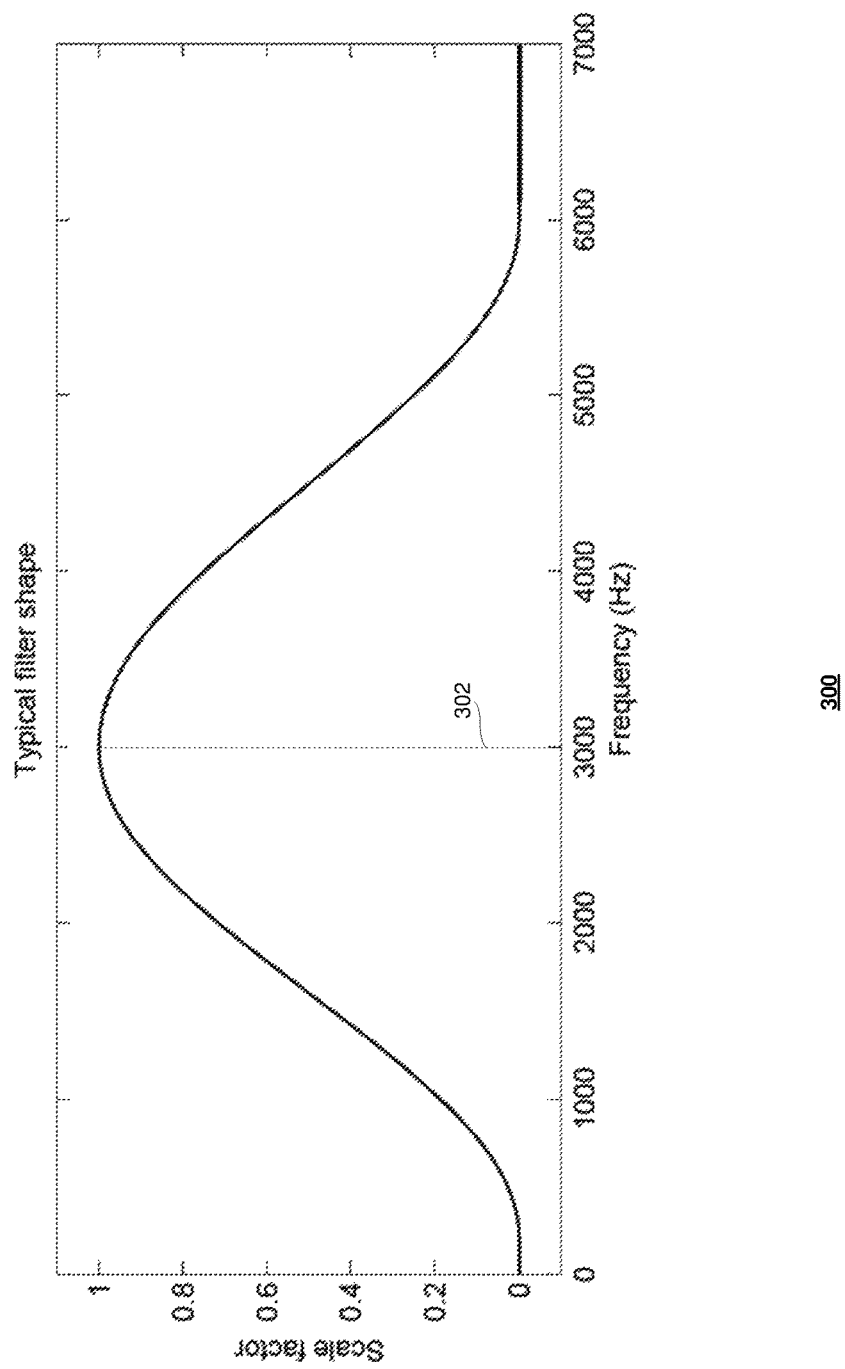
Figure 4:
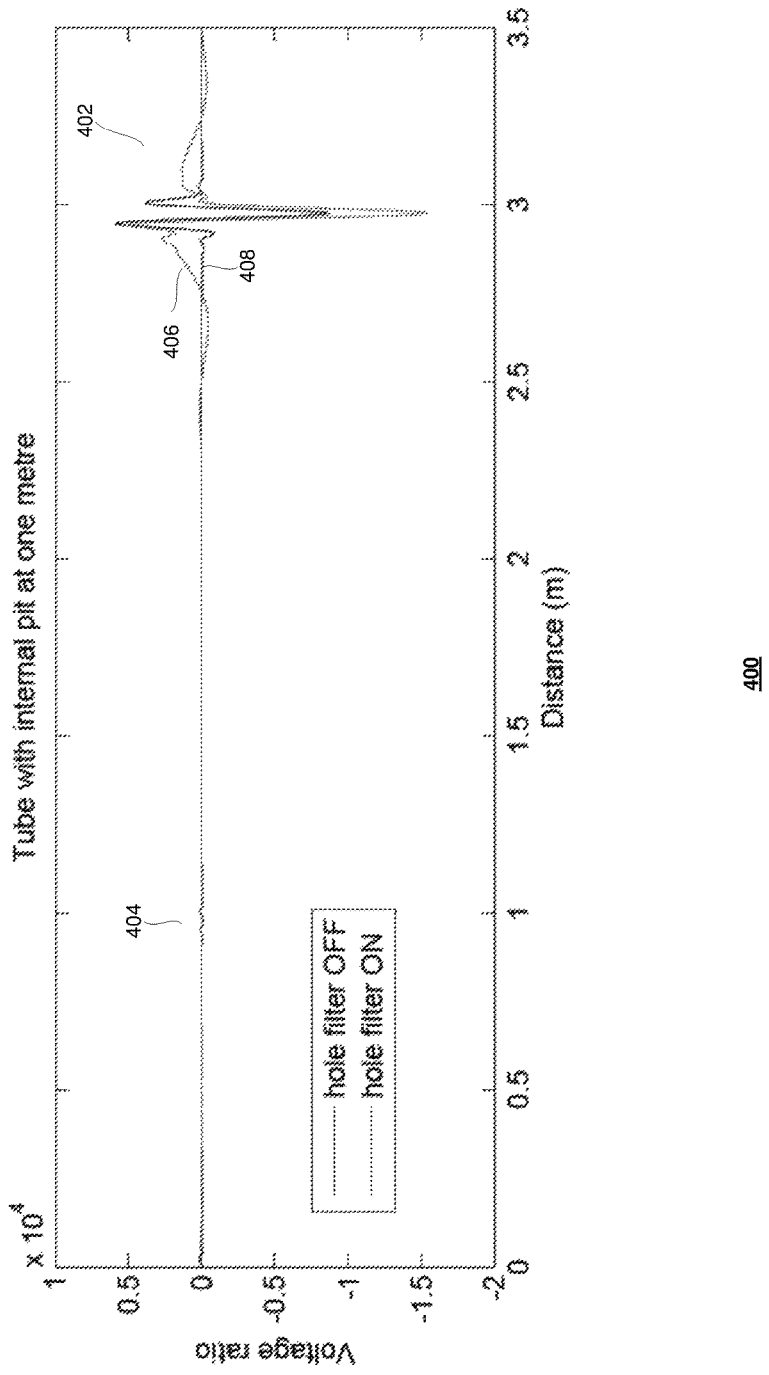
Figure 5:
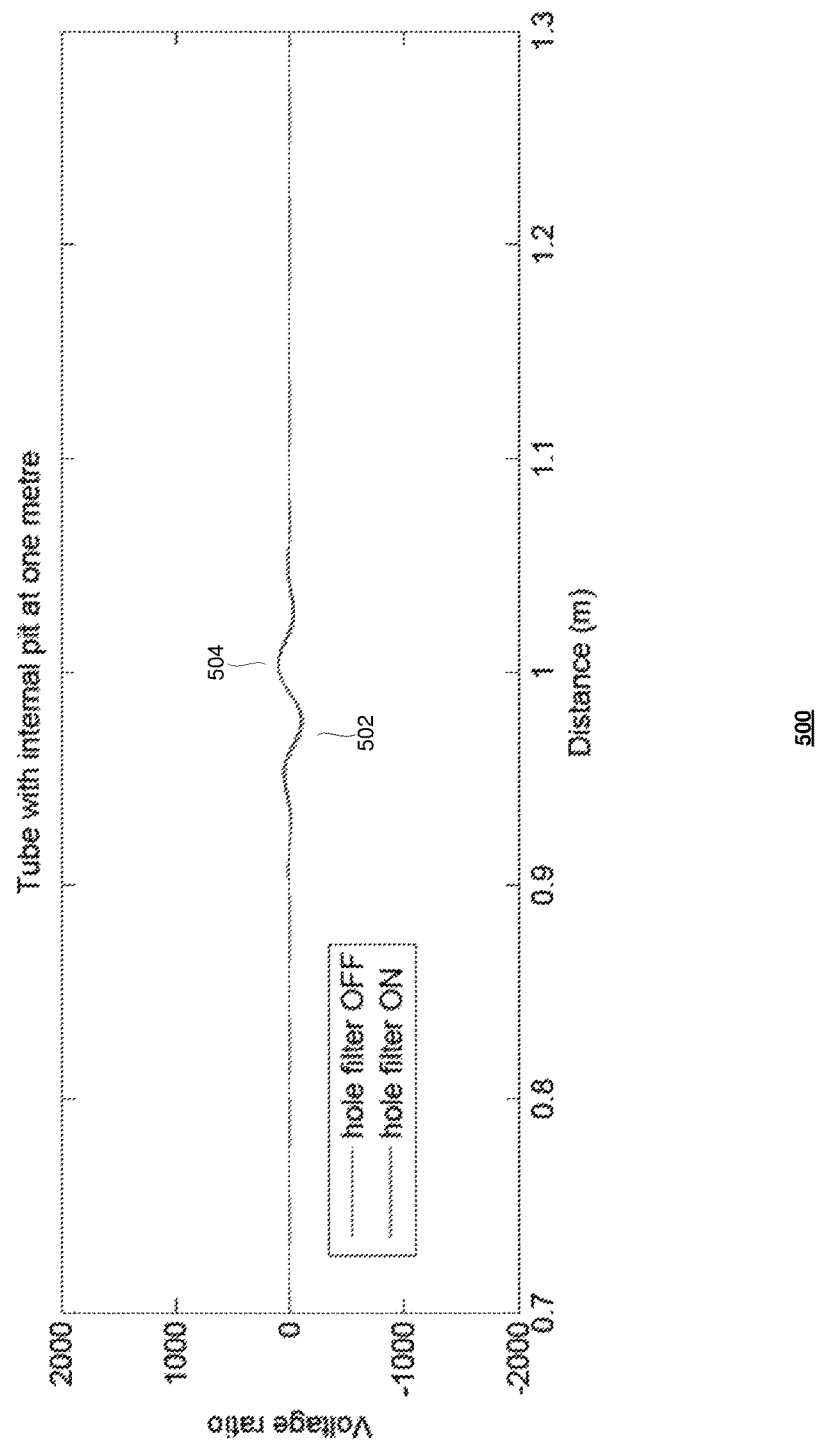
Figure 6:
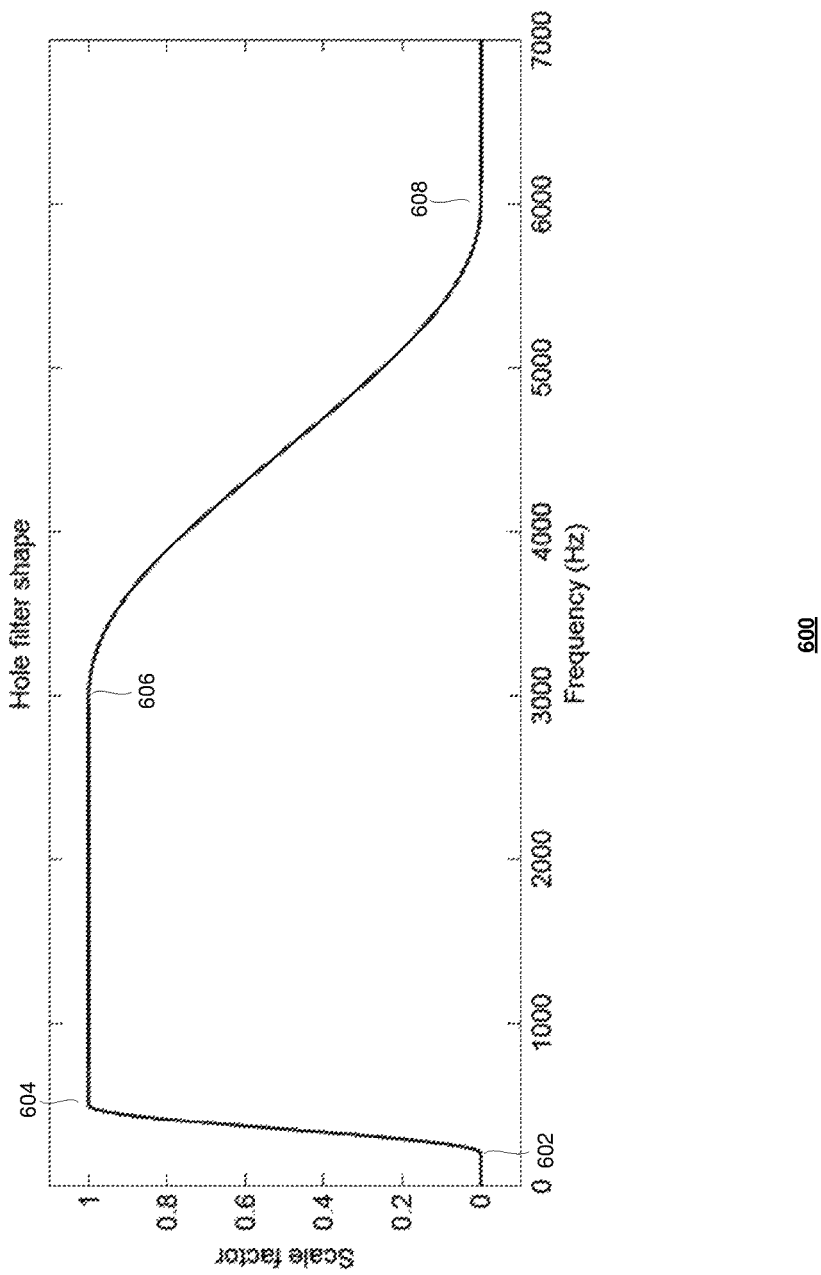
Figure 7:
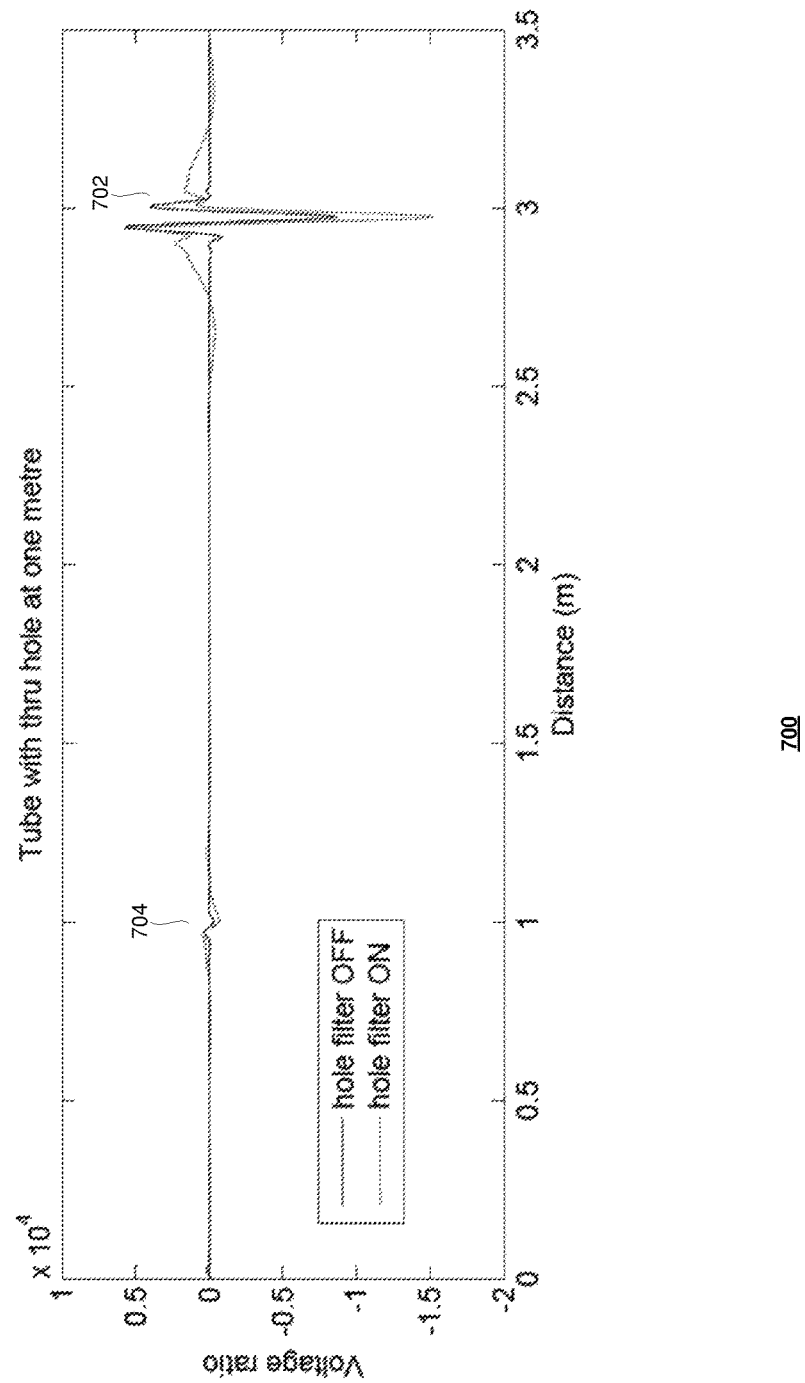
Figure 8:
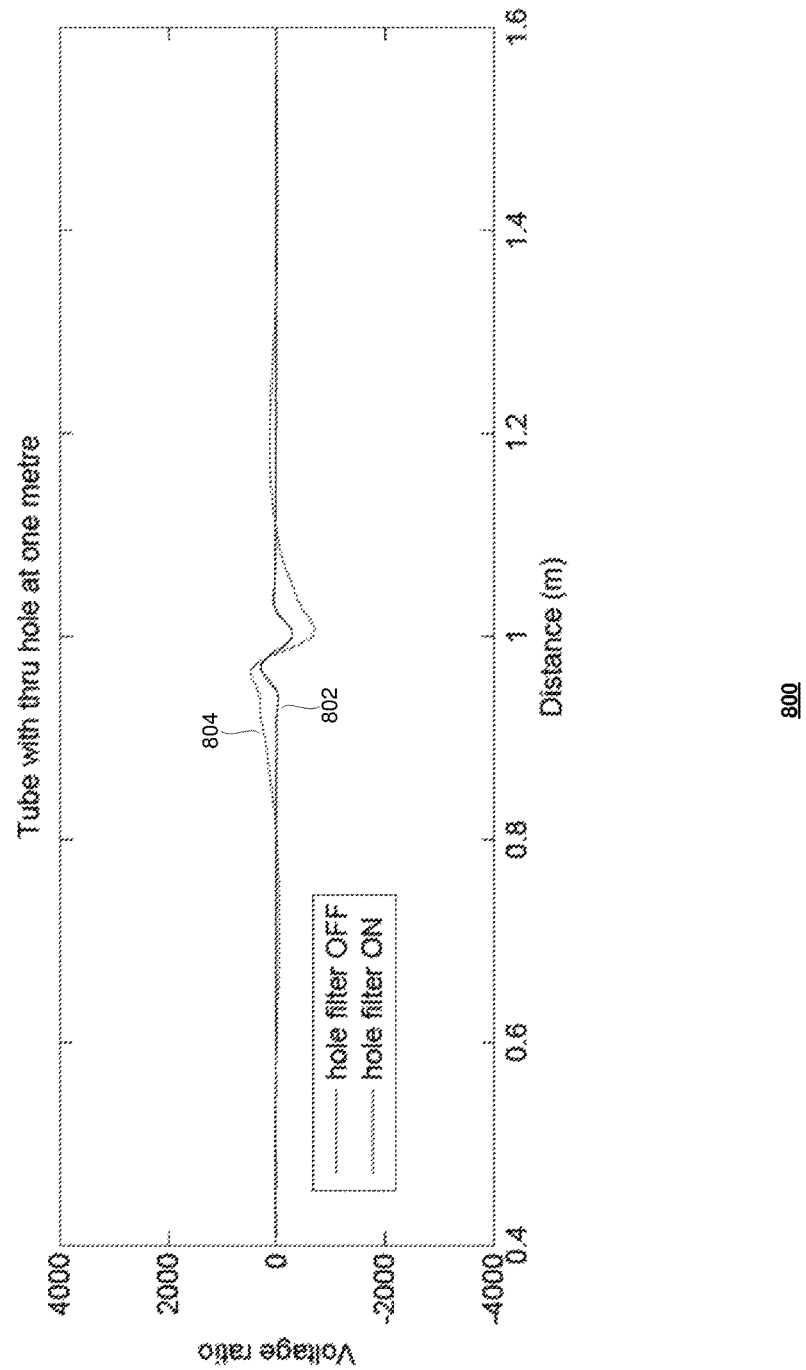
Figure 9:
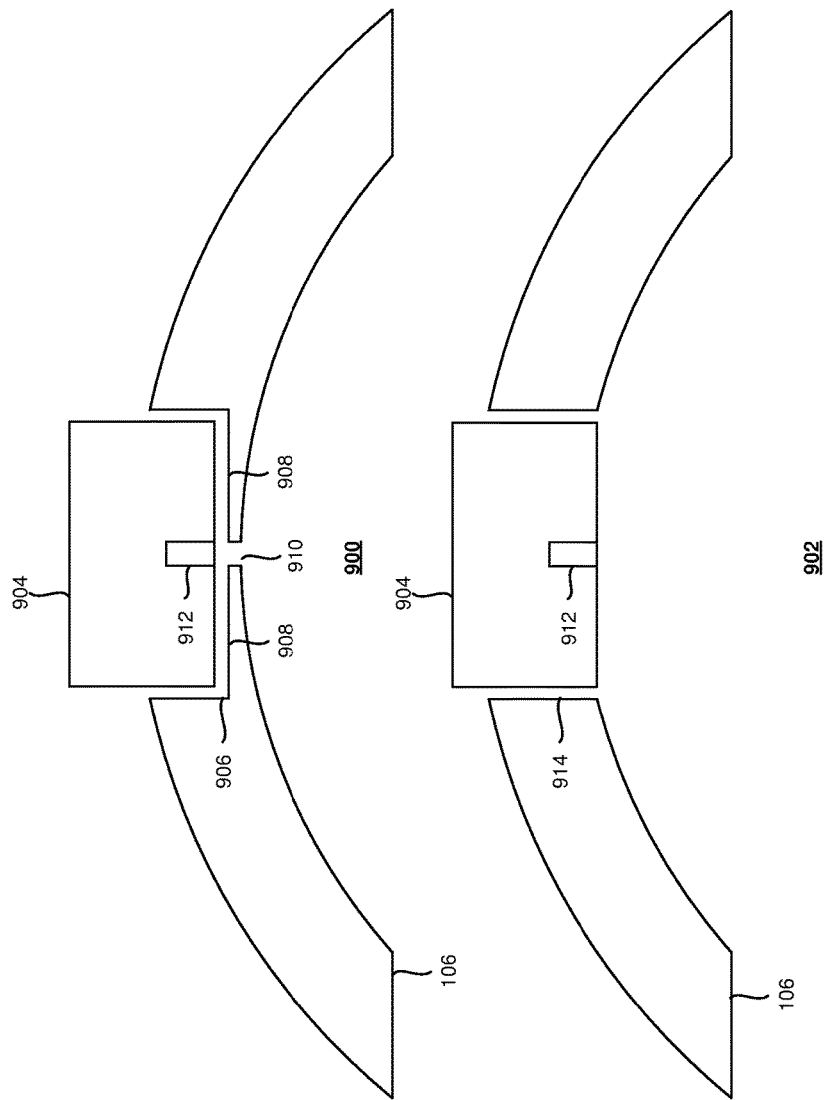
Figure 10:
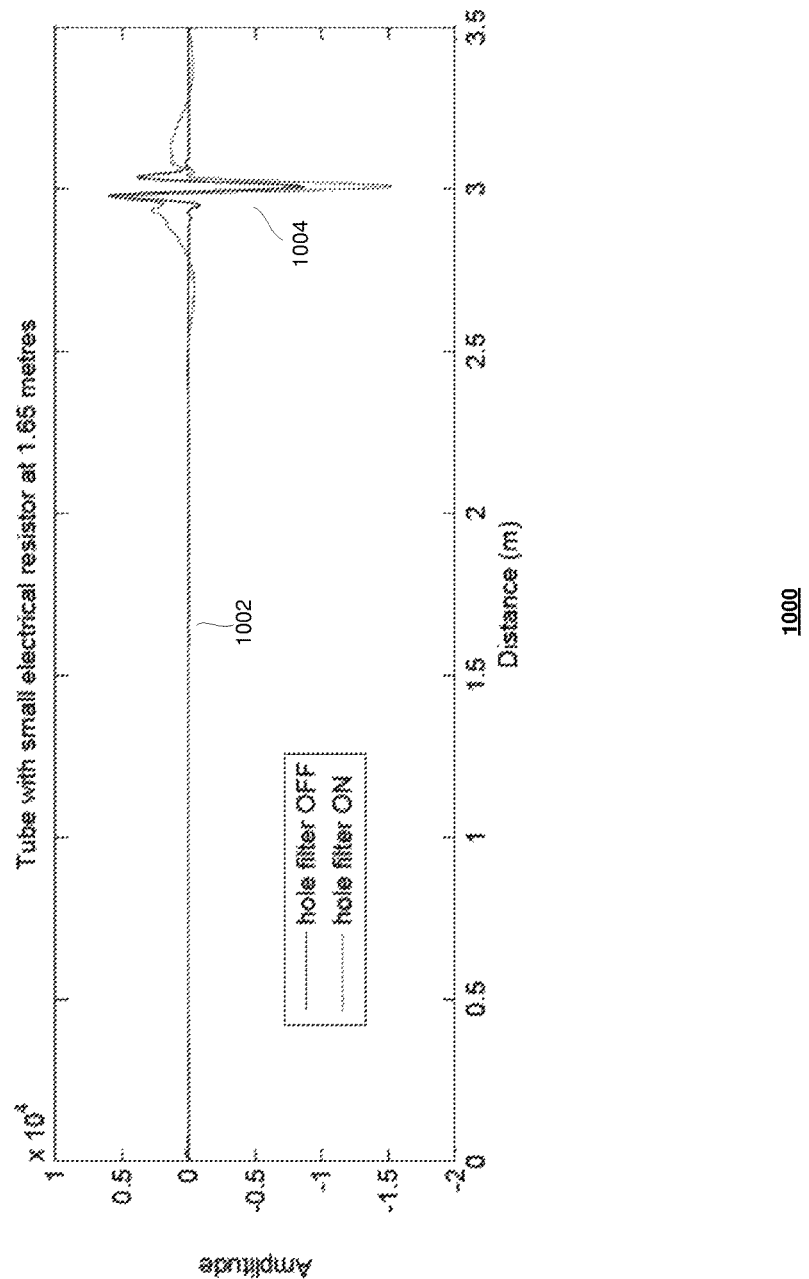
Figure 11:
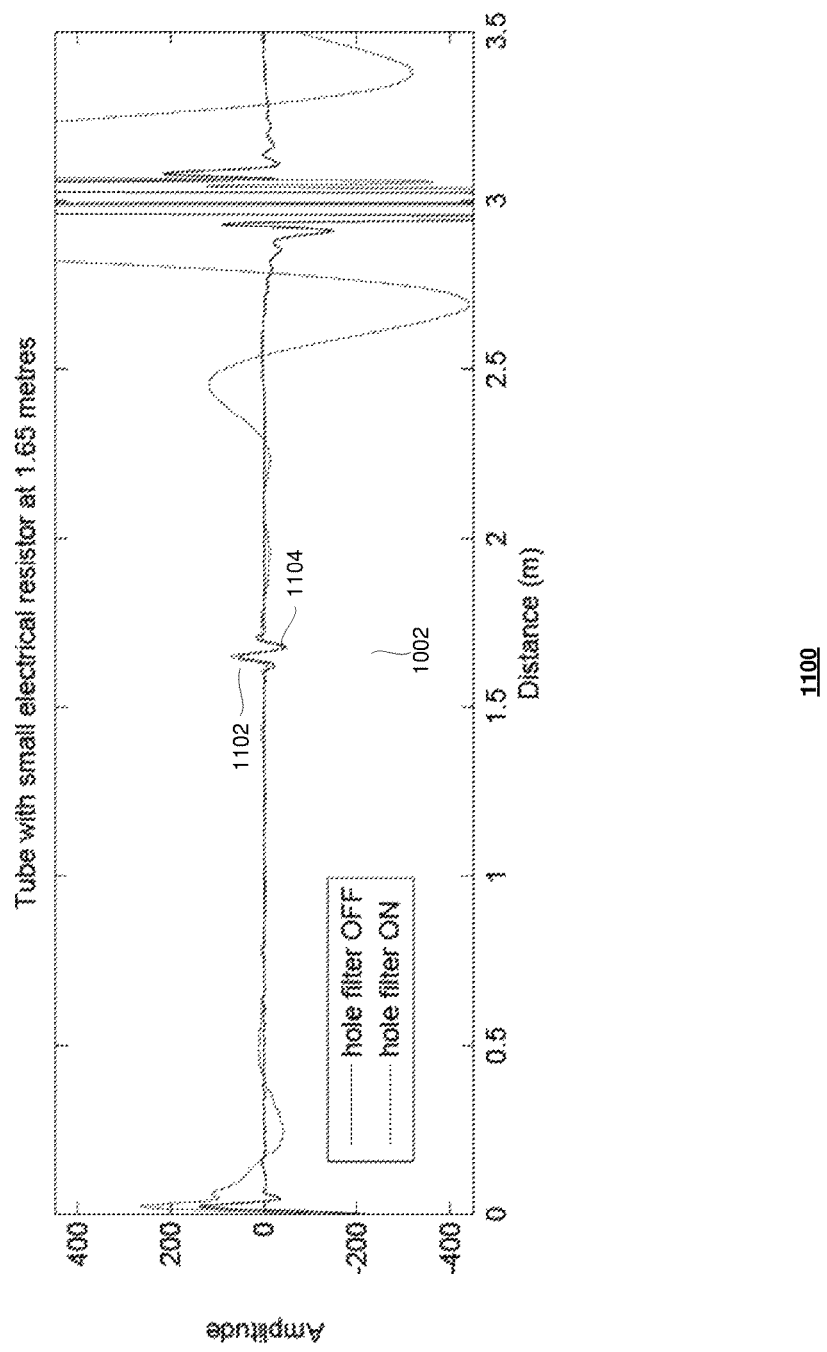

Embodiments are further described hereinafter with reference to the accompanying drawings, in which:

FIG. 1 shows a signal processing system;
FIG. 2 illustrates a signal processing flowchart;
FIG. 3 depicts a filter;
FIGS. 4 and 5 shows an acoustic impulse response associated with a pipe with a pit;
FIG. 6 shows a filter associated with hole detection;
FIGS. 7 and 8 depict an acoustic impulse response associated with a pipe with a through-hole;
FIG. 9 shows embodiments of microphone mounting or couplings; and
FIGS. 10 and 11 shows acoustic impulse responses associated with a blockage.

Referring to FIG. 1, there is shown a signal processing system 100 comprising an excitation and monitoring assembly or probe 102. The excitation and monitoring assembly 102 comprises an acoustic excitation source 104 coupled to an acoustic launch or source-tube 106 via a respective manifold 108.

In the embodiment illustrated, the acoustic excitation source 104 comprises a speaker. Embodiments use a JBL 2426J compression driver as the speaker 104. Preferably, the source 104 comprises a flat frequency response.

The acoustic launch 106 comprises a tube. Embodiments can be realised using an aluminium tube as the acoustic launch. The dimensions of the launch tube can vary according to the dimensions of the target object whose acoustic impulse response or transfer characteristics are to be determined. Embodiments can be realised in which the launch tube has one or more than one of the following characteristics: a predetermined outer diameter, such as, for example, 25.4 mm, a predetermined internal diameter such as, for example, 19 mm and a predetermined length such as, for example, 100 mm taken jointly and severally in any and all combinations. The acoustic launch 106 is adapted to accommodate a number of audio detection devices. The audio detection devices can be microphones such as, for example, a Bruel & Kjaer 4494 Delta Tron pressure field sensor, which is preferred for its size and frequency response. In the embodiment illustrated, at least a pair of microphones 110 and 112 is provided. The microphones are separated by a predetermined distance and, optionally, are axially aligned. In an embodiment, the microphones are separated by a distance of 21.3 mm. However, embodiments are not limited to such a predetermined separation. Furthermore, the microphones are coupled to the launch 106 in a manner that preferably minimises any change in acoustic impedance within the launch 106. Embodiments can be realised in which the microphones are mounted in a sealed manner within holes in the launch wall. A hot glue gun is used to fix the microphones in place and to form a seal. An alternative, or additional, mounting technique comprises mounting the microphones within grommets held within the holes of the launch tube. It will be appreciated that a seal is desirable to reduce any adverse acoustic impedance associated with the microphones or their mounts.

The launch 106 comprises first 116 and second 118 openings. The first opening 116 is disposed adjacent to the speaker 104. The first opening 116 is arranged to receive an emitted waveform (not shown) output by the speaker 104 and to couple a stimulation waveform (not shown) to a test object 120 via the second opening 118 and a respective input aperture 122 of the test object 120. For purposes of illustration only, the test object 120 is a hollow-body such as, for example, a pipe. The illustrative pipe comprises a radially expanded portion 124. However, embodiments are not limited to operating with such a test object. Embodiments can be realised that cooperate with any object to be tested. It will be appreciated that the stimulation waveform coupled to the test object will be different to the emitted waveform. It will be appreciated that the distance between the acoustic detection devices and the test object, in particular the test object's aperture, is minimised.

The microphones 110 and 112 are positioned to monitor an overall waveform. The overall waveform is the combination of the emitted wave, that is, stimulation waveform, all forward travelling waveforms and all backward travelling waveforms, which are embodiments of forwards and backwards pressure waveforms. Embodiments define a forward travelling waveform as at least one waveform propagating away from the source 104. Embodiments define a backward travelling waveform as at least one waveform propagating towards the source 104. It will be appreciated that the forwards and backwards waveforms will comprise the superposition of many reflected waveforms.

An object whose transfer function is to be determined has at least one characteristic acoustic impulse response. The at least one characteristic acoustic impulse response can be associated with at least one of an intended feature of the object or an anomaly associated with the object or be associated with the whole of the object or a part thereof. The object can comprise a hollow-body such as, for example, a pipe, a plurality of connected pipes, or one or more shaped pipes comprising one or more features such as, for example, at least one of a bend, a curved portion, an expanded section, a restricted section, an intruding section, a protruding section, a joint, a connector or coupling, a valve, another pipe or other anomaly associated with the object all taken jointly and severally in any and all combinations. Anomalies can comprise, for example, holes and other defects such as, for example, pits, corrosion, sludge, sediment, cracks, fractures and accumulations. Furthermore, other anomalies or features of interest comprise T-pieces, flanges, weld joints, sensors, devices, valves, bends, deformations, peeling coatings, inner lumen linings, absence of linings and the like. The foregoing are instances of impedance changing features or features having respective acoustic impulse responses. It will be appreciated that a pipe is a substantially elongate member.

The manifold 108 is arranged to couple the speaker 104 to the launch 106. The manifold 108 is annular. Embodiments can be realised in which a gap is presented between the speaker 104 and the launch tube. Embodiments can be realised in which such a gap is filled with acoustic foam. The width of the gap is such that no anti-resonances are created within a frequency range of interest. Embodiments can be realised in which the gap is arranged to increase attenuation that, in turn, reduces the magnitude of re-reflections within the launch 106 thereby simplifying the summation of the forward travelling waves. Furthermore, the gap distorts the re-reflected waves, that is, the forward travelling waves so that they are significantly different from the backwards travelling waves. The differences and attenuation influence the noise in the measured resultant pressure waveform(s). The launch 106 is arranged so that the excitation waveform can be launched into the object under investigation via an access or launch opening of the object. Embodiments launch the excitation waveform longitudinally into a pipe or other object via an open end of the pipe or an associated aperture.

The excitation and monitoring assembly 102 optionally comprises an amplifier 114 for amplifying the outputs of the microphones 110 and 112. The amplifier 114 can form part of the excitation and monitoring assembly 102, but embodiments are not limited to such an arrangement. Embodiments can be realised in which the amplifier 114 is separate from the excitation and monitoring assembly 102.

The speaker 104 is driven by a predetermined waveform (not shown). In a preferred embodiment, the waveform is a pseudorandom sequence such as, for example, a MLS sequence, such as, for example, a band-limited MLS sequence. Preferably, the MLS sequence is at least one of pre- and post-padded with itself. The MLS sequence is, according to some embodiments, band-limited to reduce non-linear effects of the speaker and to reduce the load on the speaker. It will be appreciated that duration of the excitation signal such as, for example, the MLS should be preferably as long as the acoustic impulse response of the object under investigation. In preferred embodiments, the MLS is converted into +1s and −1s to drive the speaker 104. Although embodiments have been described with reference to using an MLS as the excitation waveform, other embodiments can equally well use other broadband signals such as, for example, pseudo-random binary sequences, a chirp signal, a swept sine-wave, WMLS, IRS, or white noise. The signal to noise ratio improves with increasing signal length up to a predetermined point before $2^{nd}$ order modes arise or become significant.

Embodiments provide a waveform generator 126 for producing the predetermined waveform and driving the speaker 104. The waveform generator 126 is an embodiment of an excitation source. Preferably, the waveform generator 126 is realised using at least an amplifier 128 adapted to receive the predetermined waveform from a computer 130. The predetermined waveform can be provided to the waveform generator 126 either directly from the computer 130, or, optionally, via an intermediary. Preferred embodiments of such an intermediary can be realised using a data acquisition board 132 for supplying the predetermined waveform to the waveform generator 126.

The data acquisition board 132 also serves to acquire the outputs of the acoustic detection devices 110 and 112, preferably after amplification by the amplifier 114.

It will be appreciated that pressure waves generated by the speaker 104 will propagate along the launch 106 into the test object 120 via its aperture 122. When this wave, that is, the forward travelling wave, encounters a change in acoustic impedance, part of the pressure wave is reflected back towards the microphones, which are otherwise known as probes. The reflected wave, that is, the backward travelling wave, is, in turn, reflected forwards again by any changes of acoustic impedance. The resulting pressure waves continually reflect backwards and forwards until they attenuate completely. Forwards and backwards travelling waves will exist within the source-tube 106 simultaneously. The two microphones 110 and 112 can be used to record the pressures at two locations to allow the forwards and backwards travelling waves to be separated. One skilled in the art will appreciate that the resulting forwards travelling waveform is the summation of time shifted versions of the forward travelling wave. The same applies to the backwards travelling wave. By separating the overall waveform into forwards and backwards travelling waves and deconvolving the two, it is possible to determine the acoustic impulse response of the test object 120.

Referring to FIG. 2, there is shown a flowchart 200 of the steps for investigating a test object such as, for example, determining the test object's acoustic impulse response or transfer function using the signal processing system 100 described above. It will be appreciated that embodiments of the processing undertaken in one or more than one step of the flowchart 200 can be performed by the computer 130 via its processor and suitable instructions.

At step 202, the predetermined waveform for driving the speaker 104 is generated and used, at step 204, to stimulate the test object and, preferably concurrently, to record, via the data acquisition board 132, the resulting overall waveforms at the microphones such as the two microphones 110 and 112. The acquired overall waveforms are processed at step 206 to identify or extract signals of interest such processing is described below. A separation algorithm is applied at step 208 to produce forwards and backwards travelling waves. The forwards and backwards travelling waves are deconvolved at step 210 and the result of the deconvolution is processed at step 212 to produce an overall acoustic impulse response associated with the test object 120.

Each of the foregoing steps will be described in greater detail. The excitation waveform generated and output at steps 200 and 204 comprises a pseudorandom sequence. Embodiments are provided in which the excitation waveform is a cyclic pseudorandom sequence that is, preferably, at least one of post-padded and pre-padded with itself; still more preferably, both pre- and post-padded. The padding is arranged to ensure that the centre sequence of the excitation waveform is also cyclic, which at least reduces and, preferably, removes the need for time domain windowing when frequency analysis, such as, for example, FFT or DFT, is performed during at least one of the later deconvolution and filtering stages. The frequency content of the excitation signal is arranged to fall within a linear region of the speaker 104, and such that that content also falls within a substantially flat portion of the frequency response of speaker 104.

At step 206, the output from the data acquisition board 132 is used in a feedback loop 134 to estimate the delay introduced by the data acquisition board and the waveform output by the computer 130. The delay is determined by, for example, cross-correlating the output of the computer and the output of the data acquisition board. One skilled in the art will appreciate that the purpose of identifying the delay or shift in the waveform is to allow it to be taken into account when extracting the cyclic centre portion of the waveform from the signals measured by the microphones 110 and 112. Alternatively, appropriate triggering could be used to time the data acquisition. The delay and triggering are directed at ensuring that the same portion of the waveform within launch 106 is captured, which is desirable during repeated testing. The delay or triggering can also take into account at least one of any delays through the amplifier, the speaker and the microphone taken jointly and severally in any and all combinations. The foregoing is achieved by, firstly, taking into account any such delay and, secondly, by removing the pre- and post-padding thereby leaving at least one full cycle of the MLS sequence, that is, the measured or recorded signals within the launch 106 that are associated with or correspond with one full cycle of the MLS sequence, with repeatable start and end positions. In essence, step 206 is directed to being able to repeatedly/predictably process the portion of the detected signal corresponding to the excitation sequence or selectable portion or portions of the excitation sequence.

The separation algorithm applied at step 208 is arranged to transform the waveforms, $p_{x1}(t)$ and $p_{x2}(t)$, recorded by the microphones 110 and 112 into $p_{x2}^+(t+\tau)-p_{x2}^+(t-\tau)$ and $p_{x2}^-(t+\tau)-p_{x2}^-(t-\tau)$, where $p_{x2}^+(t)$ is the forward travelling wave at a selectable one of the two microphones and where $p_{x2}^-(t)$ is the backward travelling wave at the same microphone, such as, for example, microphone 112, that is, the second microphone and $\tau$ is a time shift that represents the time taken for sound to travel between the two microphones 110 and 112 in whatever medium is within the launch 106.

Assuming that there are negligible losses between the two microphones 110 and 112, and that the pressure field, $p_x(t)$, in the source-tube 106 can be described as the superposition of two one-dimensional waves, $p_x^+(t)$ and $p_x^-(t)$, propagating to the right and left respectively of axial position x at the same speed but in opposition directions, then $$p_x(t)=p_x^+(t)+p_x^-(t) \quad (1)$$

As indicated, $\tau$ is the propagation delay between the two microphones 110 and 112, such that $$p_{x2}^+(t)=p_{x1}^+(t-\tau) \quad (2)$$

$$p_{x2}^-(t)=p_{x1}^-(t+\tau) \quad (3)$$

where the subscripts x1 and x2 refer to the microphone locations. It will be appreciated that the forward, $p_x^+(t)$, and backward, $p_x^-(t)$, travelling waves are related by the acoustic impulse responses, h(t) and s(t), of the system either side of the microphones 110 and 112 such that $$p_{x2}^-(t)=p_{x2}^+(t)*h(t) \quad (4)$$

$$p_{x2}^+(t)=p_{x2}^-(t)*s(t) \quad (5)$$

where h(t) is the acoustic impulse response of the part of the system lying in the domain x>x2 and s(t) is the acoustic impulse response of the part of the system lying in the domain x<x2 and * represents convolution. Rearranging equations (1), (2) and (3) to express pressures at the measurement sites in terms of the forward and backward travelling waves at location x2 gives $$p_{x1}(t)=p_{x2}^+(t+\tau)+p_{x2}^-(t-\tau) \quad (6)$$

$$p_{x2}(t-\tau)=p_{x2}^+(t-\tau)+p_{x2}^-(t-\tau) \quad (7)$$

$$p_{x2}(t+\tau)=p_{x2}^+(t+\tau)+p_{x2}^-(t+\tau) \quad (8)$$

subtracting (7) from (6) and (6) from (8) gives $$p_{x1}(t)-p_{x2}(t-\tau)=p_{x2}^+(t+\tau)-p_{x2}^+(t-\tau) \quad (9)$$

$$p_{x2}(t+\tau)-p_{x1}(t)=p_{x2}^-(t+\tau)-p_{x2}^-(t-\tau) \quad (10)$$

Equations (9), (10) and (4) give $$h(t)*[p_{x1}(t)-p_{x2}(t-\tau)]=[p_{x2}(t+\tau)-p_{x1}(t)] \quad (11)$$

or $$h(t)*[p_{x2}^+(t+\tau)-p_{x2}^+(t-\tau)]=[p_{x2}^-(t+\tau)-p_{x2}^-(t-\tau)] \quad (12)$$

Therefore, the acoustic impulse response can be found by solving equation (11) or (12) for h(t).

Turning to equation (12), taking the FFT throughout, rearranging and then taking the IFFT gives $$h(t) = IFFT\left\{\frac{FFT[p_{x2}^-(t+\tau) - p_{x2}^-(t-\tau)]}{FFT[p_{x2}^+(t+\tau) - p_{x2}^+(t-\tau)]}\right\} \quad (13)$$

It can be appreciated that one skilled in the art does not specifically need to know the emitted waveform to be able to evaluate equation (13), which is in contrast to prior art techniques.

Applying the same process of taking the FFT, rearranging and taking the IFFT to equation 10 gives:

$$h(t) = IFFT\left\{\frac{FFT[p_{x2}(t+\tau) - p_{x1}(t)]}{FFT[p_{x1}(t) - p_{x2}(t-\tau)]}\right\} \quad (14)$$

It can be appreciated that equation (14) is expressed in terms of signals as measured by the two microphones. It will be appreciated that taking the FFT, rearranging and then taking the IFFT is an example of a system identification or deconvolution algorithm. One skilled in the art will appreciate that other system identification algorithms could be used such as, for example, a single value decomposition or truncated single value decomposition method.

Preferably, a non-zero value is added to the denominator of equation (13) or (14) to eliminate the possibility of dividing by zero. In essence, step 210 implements equation (14).

Once the acoustic impulse response h(t) has been determined, unwanted frequency content is optionally removed by filtering at step 212. The filtering is performed using a band-pass filter to remove unwanted frequencies. Embodiments are provided in which unwanted frequencies are at least those frequencies that are below a predetermined frequency such as, for example, below 200 Hz. Additionally, or alternatively, embodiments are provided in which the unwanted frequencies are at least those frequencies that are above a predetermined frequency such as, for example, 6 kHz. Preferred embodiments of such filtering are realised using a cosine shaped filter such as, for example, a slow rolling ½ cosine shaped filter that is applied in the frequency domain. For detection, in a general sense, of features of the pipe stop, pass, pass, stop bands for the band pass filter are 200 Hz, 3 kHz, 3 kHz and 6 kHz respectively. For hole detection, more low frequency content is allowed and the bands are changed to 200 Hz, 500 Hz, 3 kHz and 6 Khz respectively. It will be appreciated that the filter can be adapted according to at least one of a target object's dimensions or the launch length and diameter; both launch length and diameter. For example, lower frequency content prevails and higher frequency content diminishes with increasing pipe length. Therefore, for example, for longer pipes the stop, pass, pass, stop bands could be adapted such that the higher roll-off frequency is reduced. Consequently, an embodiment is provided with 200 Hz, 2500 Hz, 2500 Hz and 5000 Hz stop, pass, pass, stop bands. Although embodiments use a cosine shaped filter, other filters could be used to remove unwanted frequencies.

Preferably, the filter is associated with the microphone separation, that is, the inter-microphone separation. The separation algorithm implemented at step 208 introduces a phase cancellation in h(t) at $1/2\tau$ Hz. Therefore, minimising the inter-microphone distance raises the upper bounds of the useable frequency content. However, if the inter-microphone distance is too small then the differential between low frequencies measured at the microphones becomes increasingly small and thereby reduces the signal to noise ratio (SNR). Preferred embodiments use an inter-microphone distance of 21.3 mm. However, embodiments are not limited thereto. Embodiments can be realised in which other inter-microphone distances can be used. Typically, assuming the speed of sound to be 342 m/s, then the upper phase cancellation is at about 8 kHz. The separation of 21.3 mm also gives an acceptable SNR above 200 Hz. Preferred embodiments are arranged to have an inter-microphone flight time of an integer multiple of $1/f_s$ seconds,
where $f_s$ is the sampling frequency used to ensure that the separation algorithm is applicable to discrete data. More specifically, assuming the speed of sound to be 342 m/s and a predetermined sampling rate, such as, for example, 96 kHz, the flight distance of a wave between samples would be given by $\Delta l = 342/96000 = 3.56 \times 10^{-3}$.

Therefore, embodiments provide for the microphone spacing to be an integer multiple of $\Delta l$. In an embodiment the microphone spacing is $6\Delta l = 21.38 \times 10^{-3}$, which means that $\tau = 6/96 \times 10^3$. This, in turn, establishes a singularity or drop-out at $96 \times 10^3/12 = 8300$ Hz. It can be appreciated that the wave separation provides a forward (or backward) going wave minus a time delayed version of itself. If for a given frequency the time delay is equal to one wavelength, then the subtraction will cause the signal to cancel out leaving a zero response at the given frequency. Therefore, a delay of $2\tau$ would be problematical.

Referring to FIG. 3, there is shown a view 300 of a filter according to an embodiment. It can be appreciated that the filter has a predetermined centre frequency 302. The filter has a predetermined roll-off. In the embodiment shown, the centre frequency is 3 kHz and/or with a roll off factor of ¼.

Referring to FIG. 4, there is shown a view 400 of results of deriving the acoustic impulse response or transfer function of an object. In the illustrated embodiment, the object was a 3m cylindrical tube known to have a pit at 1 m. It will be appreciated that the axis are labelled as distance and voltage, but the abscissa could have equally well been label "time" since one skilled in the art appreciates that "distance" is merely a scaled version of "time" with the scaling factor being the velocity of the excitation waveform, that is, the acoustic wave. The ordinate shows acoustic impulse response amplitude.

It can be appreciated that the acoustic impulse response 400 has first 402 and second 404 features of interest. The first, larger, feature 402 of interest arises due to reflections of the acoustic waves within the tube encountered by the change in acoustic impedance caused by the open end of the tube under investigation; the other end being closed due to the excitation source. The second, smaller, feature 404 of interest arises due to a change in acoustic impedance presented by the above pit in the wall of the tube.

The view shows a pair of acoustic impulse responses; one with the acoustic impulse response determined using a filter, that is, a larger response 406, and the other without a filter, that is, the smaller response 408.

FIG. 5 shows an expanded view 500 of the portion of the response 404 shown in FIG. 4 corresponding to the pit. It can be appreciated that the change acoustic impedance exhibited by a pit in a tube reveals a drop in pressure followed by an increase in pressure as the excitation waveform passes the pit. The drop in pressure is shown at 502 and the increase in pressure is shown at 504. It can also be appreciated that the filter, which is adapted for detecting holes, makes almost no difference to the acoustic impulse response associated with the pit.

FIG. 6 shows a view 600 of a hole filter used for detecting holes in objects. As indicated above, the hole filter 600 has predetermined stop, pass, pass, stop frequencies 602 to 608. In the embodiment illustrated those frequencies are 200 Hz, 500 Hz, 3 kHz and 6 Khz respectively.

FIG. 7 shows a view 700 of acoustic impulse responses of a tube having a through-hole at 1 m. Again, it can be seen that there is a first, larger, 702 feature present at 3 m, which is due to the change in acoustic impedance presented by the open end of the tube, and a second, smaller, 704, feature due to the change in acoustic impedance presented by the through-hole at 1 m.

Referring to FIG. 8, there is shown an expanded view 800 of the portion 704 of the acoustic impulse response shown in FIG. 7 associated with the through-hole. It can be appreciated that the hole filter described with reference to FIG. 6 has a significant impact on the acoustic impulse response. The acoustic impulse response determined without the hole filter is shown at 802. It can be appreciated that a characteristic change in acoustic impedance associated with a through-hole shows an increase in pressure followed by a decrease in pressure. It can be appreciated that the acoustic impulse response 804 determined with the hole filter is different to the acoustic impulse response 802 determined without the hole filter. The second acoustic impulse response 804 has larger amplitude variations and more progressive variations in pressure. In either case, one skilled in the art can readily determine from the acoustic impulse response that a through-hole is present 1 m from an end of the tube under investigation.

Furthermore, preferred embodiments are arranged such that only first order pressure waves are monitored, since the transition frequency at which the wave within a pipe changes from the first order mode (plane wave) to the second order mode is a limiting factor in the usable frequency content.

To achieve a clean, ripple free acoustic impulse response with an acceptable SNR, several factors should preferably be taken into account such as, for example, the manifold design, the microphone fitting and the seal between the probe and the test object 120.

The manifold is arranged to ensure that the frequency content of the pressure wave passing the microphones 110 and 112 is flat. Preferred embodiments use a compression driver to function as both a speaker 104 and manifold 108. The frequency response of a compression driver is substantially flat when connected to a horn having a corresponding throat diameter. Therefore, the compression driver selected to function as the speaker and manifold has dimensions according to the dimensions of the launch or source-tube 106. The microphones 110 and 112 should have a flat frequency response over the bandwidth of interest while being of a predetermined, preferably, small size. The microphones 110 and 112 are hermetically sealed within the launch or source-tube 106.

The seal between the end of the excitation and monitoring assembly or probe 102 and the test object 120 can be realised using an adaptor. Embodiments of the adaptor comprise a flexible rubber or foam seal. The adaptor is arranged to couple the excitation waveform from the launch 106 to the pipe or other object under investigation in a way that minimises introducing significant acoustic impedance changes as a consequence of the coupling.

In the above embodiments, it will be appreciated that the transfer function of the launch 106 between the two microphones has not been taken into account, or has at least been dismissed on the assumption that the attenuation between the two microphones is small. However, embodiments can be realised in which the transfer function between the two microphones is taken into account. In such embodiments the microphones are preferably calibrated such that the transfer function, $h_{m12}(t)$ from the first microphone to the second microphone is equal to the transfer function, $h_{m21}(t)$ that relates the second microphone to the first microphone, that is, $h_{m12}(t)=h_{m21}(t)$. Therefore, equations (4) and (5) become $$p_{x2}^+(t)=p_{x1}^+(t)*h_{m12}(t) \tag{15}$$

$$p_{x1}^-(t)=p_{x2}^-(t)*h_{m12}(t) \tag{16}$$

Defining $h_{m12}^{-1}(t)$ as the inverse filter or transfer function associated with $h_{m21}(t)$, equation (16) can be rearranged as $$p_{x2}^-(t)=p_{x1}^-(t)*h_{m12}^{-1}(t) \tag{17}$$

Such that equations (6), (7) and (8) can be expressed in terms of the transfer functions $h_{m12}(t)$ and $h_{m12}^{-1}(t)$ to give $$p_{x1}(t)=p_{x2}^+(t)*h_{m12}^{-1}(t)+p_{x2}^-(t)*h_{m12}(t) \tag{18}$$

$$p_{x2}(t)*h_{m12}(t)=p_{x2}^+(t)*h_{m12}(t)p_{x2}^-(t)*h_{m12}(t) \tag{19}$$

$$p_{x2}(t)*h_{m12}^{-1}(t)=p_{x2}^+(t)*h_{m12}^{-1}(t)+p_{x2}^-(t)*h_{m12}^{-1}(t) \tag{20}$$

Subtracting equation (19) from equation (18) and equation (18) from equation (20) gives $$p_{x1}(t)-p_{x2}(t)*h_{m12}(t)=p_{x2}^+(t)*h_{m12}^{-1}(t)-p_{x2}^+(t)*h_{m12}(t) \tag{21}$$

$$p_{x2}(t)*h_{m12}^{-1}(t)-p_{x1}(t)=p_{x2}^-(t)*h_{m12}^{-1}(t)-p_{x2}^-(t)*h_{m12}(t) \tag{22}$$

such that equations (21), (22) and (6) give $$h(t)*[p_{x1}(t)-p_{x2}(t)*h_{m12}(t)]=[p_{x2}(t)*h_{m12}^{-1}(t)-p_{x1}(t)] \tag{23}$$

It can be appreciated that solving, by deconvolution, for h(t) gives, using frequency domain techniques, $$h(t) = IFFT\left[\frac{FFT[p_{x2}(t)*h_{m12}^{-1}(t) - p_{x1}(t)]}{FFT[p_{x1}(t) - p_{x2}(t)*h_{m12}(t)]}\right] \tag{24}$$

Referring to FIG. 9, there is shown first 900 and second 902 embodiments for mounting microphones 904 within the launch 106. The first embodiment 900 mounts a microphone 904 within a recess 906 in the wall of the launch 106. The recess 902 does not completely extend through the launch wall, but leaves a recess floor 908 for supporting the microphone 904. The recess floor 908 has an aperture 910 through which pressure waves can pass. The aperture 910 is disposed adjacent to an active portion 912 of the microphone 904, that is, the portion of the microphone that is most sensitive.

The second embodiment 902 mounts the microphone 904 within a through-hole 914 of the launch 106. Care is taken when mounting the microphone 904 in such an arrangement so that the acoustic impedance created by the wall-microphone-wall transition is reduced and preferably minimised.

It can be appreciated that the first embodiment 900 has a reduced wall-microphone-wall characteristic acoustic impedance as compared to the second embodiment 902.

Referring to FIG. 10, there is shown a plot 1000 an acoustic impulse response of a tube containing a very small blockage. This plot 1000 provides an indication of the exceptional sensitivity of embodiments. It can be appreciated that there is an anomaly 1002 present at a distance of 1.65 m from the launch end of the tube. The anomaly was a very small resistor within the tube. The large anomaly 1004 is the open end of the tube.

Referring to FIG. 11, there is shown an expanded view 1100 of the portion 1002 of the acoustic impulse response 1000 shown in FIG. 10. The portion of the acoustic impulse response or anomaly 1002 associated with a blockage is characterised by a rise 1102 in the acoustic impulse response followed by a fall 1104 in the acoustic impulse response. A blockage presents an increase in acoustic impedance followed by a fall in acoustic impedance. Again, two plots are shown; one with a filter ON (the smaller plot) and the other with the filter OFF (the larger plot).

Embodiments find application in inspecting heat exchangers, for example, in which many pipes carry a fluid at respective temperatures that are regulated by an external fluid at another temperature.

It will be appreciated that embodiments can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape or the like. It will be appreciated that the storage devices and storage media are embodiments of machine-readable storage that are suitable for storing a program or programs comprising instructions that, when executed, implement embodiments. Accordingly, embodiments provide machine executable code for implementing a system, device or method as described herein or as claimed herein and machine readable storage storing such a program. Still further, such programs may be conveyed electronically via any medium such as a communication signal carried over a wired or wireless connection and embodiments suitably encompass the same.

Advantageously, embodiments use acoustic reflections due to changes in acoustic impedance, howsoever caused, and notwithstanding the change being an increase or decrease, in detecting leakages from, and blockages within, or any other anomaly associated with a test object, such as, for example, a pipe or pipe network, as well as ingress of matter into the pipe or pipe network or damage to a pipe caused by, for example, deformations, sediment or corrosion.

Embodiments are also provided according to any one or more of the following clauses.

Claus 1: A pipe inspection method to identify a characteristic acoustic impedance associated with a pipe; the method comprising the steps of
resolving a plurality of measured resultant pressure waveforms, $p_{x1}(t)$, $p_{x2}(t)$, . . . , $p_{xn}(t)$ and $p_{x2}(t)$, associated with the pipe into a number of associated waveforms; the associated waveforms being a function of the plurality of measured resultant pressure waveforms measured at respective positions; the plurality of measured resultant pressure waveforms representing measurements by a plurality of acoustic detection devices positioned at the respective positions of a launch body for exciting the pipe using an excitation waveform;
deriving the impulse response, h(t), or transfer function of the pipe from said at least a pair associated waveforms; the impulse response bearing the characteristic acoustic impedance associated with the pipe.

Clause 2: A method as claimed in clause 1 further comprising exciting the pipe using the excitation waveform via the launch body.

Clause 3. A method as claimed in any preceding clause further comprising taking a plurality of measurements via the acoustic detection devices; the plurality of measured resultant pressure waveforms being associated with the plurality of measurements.

Clause 4. A method as claimed in any preceding clause further comprising filtering the plurality of measured resultant pressure waveforms prior to said resolving.

Clause 5. A method as claimed in clause 4, wherein the step of filtering applies one or more than one filter associated with a possible characteristic acoustic impedance.

Clause 6. A method as claimed in any preceding clause wherein the step of resolving the plurality of measured resultant pressure waveforms into a number of associated waveforms comprises resolving the plurality of measured resultant pressure waveforms into a number of associated waveforms representing differences between the measured resultant pressure waveforms.

Clause 7. A method as claimed in clause 6, wherein the differences between the measured resultant pressure waveforms have an associated linear function or represent time shifted versions of the measured resultant pressure waveforms.

Clause 8. A method as claimed in clause 7 wherein the linear function or differences take the form $$f(p(t))=p(t+\tau)-p(t-\tau)$$

where
p(t) represents a measured resultant pressure waveform at time t; and
$\tau$ is associated with the separation between acoustic measuring devices.

Clause 9. A method as claimed in any preceding claim, wherein the step of deriving the impulse response comprises evaluating h(t) from $$h(t)*[p_{x1}(t)-p_{x2}(t-\tau)]=[p_{x2}(t+\tau)-p_{x1}(t)].$$

Clause 10. A method as claimed in clause 9, wherein the step of deriving the impulse response comprises evaluating $$h(t) = IFFT\left\{\frac{FFT[p_{x2}(t+\tau)-p_{x1}(t)]}{FFT[p_{x1}(t)-p_{x2}(t-\tau)]}\right\}$$

where FFT represents a Fourier Domain Transform and IFFT represents an Inverse Fourier Domain Transform.

Clause 11. A method as claimed in any preceding claim, wherein the step of deriving the impulse response comprises evaluating h(t) from $$h(t)*[p_{x1}(t)-p_{x2}(t)*h_{m12}(t)]=[p_{x2}(t)*h_{m12}^{-1}(t)-p_{x1}(t)].$$

Clause 12. A method as claimed in clause 11, wherein the step of deriving the impulse response comprises evaluating $$h(t) = IFFT\left[\frac{FFT[p_{x2}(t)*h_{m12}^{-1}(t)-p_{x1}(t)]}{FFT[p_{x1}(t)-p_{x2}(t)*h_{m12}(t)]}\right]$$

where FFT represents a Fourier Domain Transform and IFFT represents an Inverse Fourier Domain Transform, $h_{m12}(t)$ represents the transfer function between the acoustic detection devices at said respective positions and $h_{m12}^{-1}(t)$ is the inverse of $h_{m12}(t)$.

Clause 13. A method as claimed in of clauses 1 to 8, wherein the step of deriving the impulse response comprises evaluating h(t) from $$h(t)*[p_{x2}^{+}(t+\tau)-p_{x2}^{+}(t-\tau)]=[p_{x2}^{-}(t+\tau)-p_{x2}^{-}(t-\tau)].$$

Clause 14. A method as claimed in clause 13, wherein the step of deriving the impulse response comprises evaluating $$h(t) = IFFT\left\{\frac{FFT[p_{x2}^{-}(t+\tau)-p_{x2}^{-}(t-\tau)]}{FFT[p_{x2}^{+}(t+\tau)-p_{x2}^{+}(t-\tau)]}\right\}.$$

where FFT represents a Fourier Domain Transform and IFFT represents an Inverse Fourier Domain Transform.

Clause 15. A method as claimed in any preceding claim, wherein the step of deriving the impulse response comprises evaluating h(t) from $$h(t)*[p_{x2}^{+}(t)*h_{m12}^{-1}(t)-p_{x2}^{+}(t)*h_{m12}(t)]=[p_{x2}^{-}(t)*h_{m12}^{-1}(t)-p_{x2}^{-}(t)*h_{m12}(t)].$$

Clause 16. A method as claimed in clause 15, wherein the step of deriving the impulse response comprises evaluating $$h(t) = IFFT\left[\frac{FFT[p_{x2}^{-}(t)*h_{m12}^{-1}(t)-p_{x2}^{-}(t)*h_{m12}(t)]}{FFT[p_{x2}^{+}(t)*h_{m12}^{-1}(t)-p_{x2}^{+}(t)*h_{m12}(t)]}\right]$$

where FFT represents a Fourier Domain Transform and IFFT represents an Inverse Fourier Domain Transform, $h_{m12}(t)$ represents the transfer function between the acoustic detection devices at said respective positions and $h_{m12}^{-1}(t)$ is the inverse of $h_{m12}(t)$.

Clause 17. A pipe inspection kit comprising
a launch tube bearing a plurality of acoustic detection devices;
an excitation source for producing an excitation waveform to be launched into a test object using the launch tube; and
a data processor adapted to implement a method as claimed in any of clauses 1 to 16.

Clause 18. A pipe inspection system for detecting a feature of a pipe; the system comprising a processor; the processor being adapted to
resolve a plurality of measured resultant pressure waveforms, $p_{x1}(t)$, $p_{x2}(t)$, ..., $p_{xn}(t)$ and $p_{x2}(t)$, associated with the pipe into a number of associated waveforms; the associated waveforms being a function of the plurality of measured resultant pressure waveforms measured at respective positions; the plurality of resultant pressure waveforms representing measurements by a plurality of acoustic detection devices positioned at the respective positions of a launch body for exciting the pipe using an excitation waveform;
derive the impulse response, h(t), or transfer function of the test object from said at least a pair associated waveforms.

Clause 19. A system as claimed in clause 18 further comprising an excitation source for exciting the pipe using the excitation waveform via the launch body.

Clause 20. A system as claimed in any of clauses 18 to 19 further comprising a sampler arranged to take a plurality of measurements via the acoustic detection devices; the plurality of measured resultant pressure waveforms being associated with the plurality of measurements.

Clause 21. A system as claimed in any of clauses 18 to 20 further comprising a filter arranged to filter the plurality of measured resultant pressure waveforms prior to said resolving.

Clause 22. A system as claimed in clause 21, wherein the filter is arranged to apply one or more than one filter associated with a possible characteristic acoustic impedance.

Clause 23. A system as claimed in any of clauses 18 to 22 wherein the processor is arranged to resolve the plurality of measured resultant pressure waveforms into a number of associated waveforms comprises resolving the plurality of measured resultant pressure waveforms into a number associated linear waveforms representing differences between the measured resultant pressure waveforms.

Clause 24. A system as claimed in clause 23, wherein the differences between measured resultant pressure waveforms have an associated linear function or represent time shifted versions of the measured resultant pressure waveforms.

Clause 25. A system as claimed in clause 24 wherein the linear function or differences take the form $$f(p(t))=p(t+\tau)-p(t-\tau)$$

where
p(t) represents a measured resultant pressure waveform at time t; and
$\tau$ is associated with the separation between acoustic measuring devices.

Clause 26. A system as claimed in any of clauses 18 to 25, wherein the processor is arranged to derive the impulse response comprises evaluating h(t) from $$h(t)*[p_{x1}(t)-p_{x2}(t-\tau)]=[p_{x2}(t+\tau)-p_{x1}(t)].$$

Clause 27. A system as claimed in clause 26, wherein the processor is arranged to derive the impulse response comprises evaluating $$h(t) = IFFT\left\{\frac{FFT[p_{x2}(t+\tau) - p_{x1}(t)]}{FFT[p_{x1}(t) - p_{x2}(t-\tau)]}\right\}$$

where FFT represents a Fourier Domain Transform and IFFT represents an Inverse Fourier Domain Transform.

Clause 28. A system as claimed in any of clauses 18 to 27, wherein the processor is arranged to derive the impulse response comprises evaluating h(t) from $$h(t)*[p_{x1}(t)-p_{x2}(t)*h_{m12}(t)]=[p_{x2}(t)*h_{m12}^{-1}(t)-p_{x1}(t)].$$

Clause 29. A system as claimed in clause 28, wherein the processor is arranged to derive the impulse response comprises evaluating $$h(t) = IFFT\left[\frac{FFT[p_{x2}(t)*h_{m12}^{-1}(t) - p_{x1}(t)]}{FFT[p_{x1}(t) - p_{x2}(t)*h_{m12}(t)]}\right]$$

where FFT represents a Fourier Domain Transform and IFFT represents an Inverse Fourier Domain Transform, $h_{m12}(t)$ represents the transfer function between the acoustic detection devices at said respective positions and $h_{m12}^{-1}(t)$ is the inverse of $h_{m12}(t)$.

Clause 30. A system as claimed in of clauses 18 to 25, wherein the processor adapted to derive the impulse response comprises evaluating h(t) from $$h(t)*[p_{x2}^{+}(t+\tau)-p_{x2}^{+}(t-\tau)]=[p_{x2}^{-}(t+\tau)-p_{x2}^{-}(t-\tau)].$$

Clause 31. A system as claimed in clause 30, wherein processor adapted to derive the impulse response comprises evaluating $$h(t) = IFFT\left\{\frac{FFT[p_{x2}^{-}(t+\tau) - p_{x2}^{-}(t-\tau)]}{FFT[p_{x2}^{+}(t+\tau) - p_{x2}^{+}(t-\tau)]}\right\}.$$

where FFT represents a Fourier Domain Transform and IFFT represents an Inverse Fourier Domain Transform.

Clause 32. A system as claimed in any of clauses 18 to 25, wherein processor adapted to derive the impulse response is adapted to evaluate h(t) from $$h(t)*[p_{x2}^{+}(t)*h_{m12}^{-1}(t)-p_{x2}^{+}(t)*h_{m12}(t)]=[p_{x2}^{-}(t)*h_{m12}^{-1}(t)-p_{x2}^{-}(t)*h_{m12}(t)].$$

Clause 33. A system as claimed in clause 32, wherein processor adapted to derive the impulse response adapted to evaluate $$h(t) = IFFT\left[\frac{FFT[p_{x2}^{-}(t)*h_{m12}^{-1}(t) - p_{x2}^{-}(t)*h_{m12}(t)]}{FFT[p_{x2}^{+}(t)*h_{m12}^{-1}(t) - p_{x2}^{+}(t)*h_{m12}(t)]}\right]$$

where FFT represents a Fourier Domain Transform and IFFT represents an Inverse Fourier Domain Transform, $h_{m12}(t)$ represents the transfer function between the acoustic detection devices at said respective positions and $h_{m12}^{-1}(t)$ is the inverse of $h_{m12}(t)$.

Clause 34. A method or system as claimed in any preceding claim, further comprising providing, or the processing being adapted to provide, an indication of the location within the pipe of the characteristic impedance.

Clause 35. Machine-readable instructions arranged, when executed, to implement a method as claimed in any of clauses 1 to 16.

Clause 36. Machine-readable storage storing machine-readable instructions as claimed in clause 35.

The word "pipe" is not intended to be limiting. The term is used to encompass objects having a cavity or bore, such as, for example, those associated with elongate bodies. Such elongate bodies can comprise ducting, conduits, tubes, hoses, flues and the like. The foregoing are embodiments of a hollow body.

The invention claimed is:

1. A pipe inspection method to identify characteristic acoustic impedance associated with a pipe; the method comprising the steps of
resolving a plurality of measured resultant pressure waveforms, $p_{x1}(t)$, $p_{x2}(t)$, ..., $p_{xn}(t)$ and $p_{x2}(t)$, associated with the pipe into a number of associated waveforms; the number of associated waveforms being a function of the plurality of measured resultant pressure waveforms measured at respective positions; the plurality of measured resultant pressure waveforms representing measurements by a plurality of acoustic detection devices positioned at the respective positions of a launch body for exciting the pipe using an excitation waveform;
deriving one or both of an impulse response, h(t), of the pipe and a corresponding transfer function of the pipe from the number of associated waveforms; the one or both of the impulse response and the transfer function bearing the characteristic acoustic impedance associated with the pipe, wherein the step of deriving the one or both of the impulse response and the transfer function comprises evaluating h(t) from $h(t)*[p_{x1}(t)-p_{x2}(t)*h_{m12}(t)]=[p_{x2}(t)*h_{m12}^{-1}(t)-p_{x1}(t)]$, where $h_{m12}(t)$ represents the transfer function between a first and second acoustic detection devices of the plurality of acoustic detection devices.

2. The method of claim 1, further comprising exciting the pipe using the excitation waveform via the launch body.

3. The method of claim 1, further comprising taking a plurality of measurements via the acoustic detection devices; the plurality of measured resultant pressure waveforms being associated with the plurality of measurements.

4. The method of claim 1, further comprising filtering the plurality of measured resultant pressure waveforms prior to said resolving.

5. The method of claim 4, wherein the step of filtering applies one or more than one filter associated with a possible characteristic acoustic impedance.

6. The method of claim 1, wherein the step of resolving the plurality of measured resultant pressure waveforms into the number of associated waveforms comprises resolving the plurality of measured resultant pressure waveforms into the number of associated waveforms representing differences between the measured resultant pressure waveforms.

7. The method of claim 6, wherein the differences between the measured resultant pressure waveforms have an associated linear function or represent time shifted versions of the measured resultant pressure waveforms.

8. The method of claim 7, wherein the linear function or differences take the form $$f(p(t))=p(t+\tau)-p(t-\tau)$$

where
p(t) represents a measured resultant pressure waveform at time t; and
$\tau$ is associated with the separation between acoustic measuring devices.

9. The method of claim 1, wherein the step of deriving the one or both of the impulse response and the transfer function comprises evaluating h(t) from $h(t)*[p_{x1}(t)-p_{x2}(t-\tau)]=[p_{x2}(t+\tau)-p_{x1}(t)]$.

10. The method of claim 9, wherein the step of deriving the one or both of the impulse response and the transfer function comprises evaluating $$h(t) = IFFT\left\{\frac{FFT[p_{x2}(t+\tau)-p_{x1}(t)]}{FFT[p_{x1}(t)-p_{x2}(t-\tau)]}\right\}$$

where FFT represents a Fourier Domain Transform and IFFT represents an Inverse Fourier Domain Transform.

11. The method of claim 1, wherein the step of deriving the one or both of the impulse response and the transfer function comprises evaluating $$h(t) = IFFT\left[\frac{FFT[p_{x2}(t)*h_{m12}^{-1}(t)-p_{x1}(t)]}{FFT[p_{x1}(t)-p_{x2}(t)*h_{m12}(t)]}\right]$$

where FFT represents a Fourier Domain Transform and IFFT represents an Inverse Fourier Domain Transform, $h_{m12}(t)$ represents the transfer function between the acoustic detection devices at said respective positions and $h_{m12}^{-1}(t)$ is the inverse of $h_{m12}(t)$.

12. The method of claim 1, wherein the step of deriving the one or both of the impulse response and the transfer function comprises evaluating h(t) from $h(t)*[p_{x12}^{+}(t+\tau)-p_{x2}^{+}(t-\tau)]=[p_{x2}^{-}(t+\tau)-p_{x2}^{-}(t-\tau)]$.

13. The method of claim 12, wherein the step of deriving the one or both of the impulse response and the transfer function comprises evaluating $$h(t) = IFFT\left\{\frac{FFT[p_{x2}^{-}(t+\tau)-p_{x2}^{-}(t-\tau)]}{FFT[p_{x2}^{+}(t+\tau)-p_{x2}^{+}(t-\tau)]}\right\}$$

where FFT represents a Fourier Domain Transform and IFFT represents an Inverse Fourier Domain Transform.

14. The method of claim 1, wherein the step of deriving one or both of the impulse response and the transfer function comprises evaluating h(t) from $h(t)*[p_{x2}^{+}(t)*h_{m12}^{-1}(t)-p_{x2}^{+(t)*h}{}_{m12}(t)]=[p_{x2}^{-}(t)*h_{m12}^{-1}(t)-p_{x2}^{-(t)*h}{}_{m12}(t)]$.

15. The method of claim 14, wherein the step of deriving the one or both of the impulse response and the transfer function comprises evaluating $$h(t) = IFFT\left[\frac{FFT[p_{x2}^{-}(t)*h_{m12}^{-1}(t)-p_{x2}^{-}(t)*h_{m12}(t)]}{FFT[p_{x2}^{+}(t)*h_{m12}^{-1}(t)-p_{x2}^{+}(t)*h_{m12}(t)]}\right]$$

where FFT represents a Fourier Domain Transform and IFFT represents an Inverse Fourier Domain Transform, $h_{m12}(t)$ represents the transfer function between the acoustic detection devices at said respective positions and $h_{m12}^{-1}(t)$ is the inverse of $h_{m12}(t)$.

16. A pipe inspection kit comprising
a launch tube bearing a plurality of acoustic detection devices;
an excitation source for producing an excitation waveform to be launched into a test object using the launch tube; and
a data processor adapted to
resolve a plurality of measured resultant pressure waveforms, $p_{x1}(t)$, $p_{x2}(t)$, ..., $p_{xn}(t)$ and $p_{x2}(t)$, associated with the pipe into a number of associated waveforms; the number of associated waveforms being a function of the plurality of measured resultant pressure waveforms measured at respective positions; the plurality of measured resultant pressure waveforms representing measurements by a plurality of acoustic detection devices positioned at the respective positions of a launch body for exciting the pipe using an excitation waveform;
derive one or both of an impulse response, h(t), of the pipe and a corresponding transfer function of the pipe from the number of associated waveforms; the one or both of the impulse response and the transfer function bearing the characteristic acoustic impedance associated with the pipe, wherein the step of deriving the one or both of the impulse response and the transfer function comprises evaluating h(t) from $h(t)*[p_{x1}(t)-p_{x2}(t)*h_{m12}(t)]=[p_{x2}(t)*h_{m12}^{-1}(t)-p_{x1}(t)]$, where $h_{m12}(t)$ represents the transfer function between a first and second acoustic detection devices of the plurality of acoustic detection devices.

17. A pipe inspection system for detecting a feature of a pipe; the system comprising a processor, the processor being adapted to
resolve a plurality of measured resultant pressure waveforms, $p_{x1}(t)$, $p_{x2}(t)$, ..., $p_{xn}(t)$ and $p_{x2}(t)$, associated with the pipe into a number of associated waveforms; the number of associated waveforms being a function of the plurality of measured resultant pressure waveforms measured at respective positions; the plurality of resultant pressure waveforms representing measurements by a plurality of acoustic detection devices positioned at the respective positions of a launch body for exciting the pipe using an excitation waveform;
derive one or both of an impulse response, h(t), of the test object and a corresponding transfer function of the test object from the number of associated waveforms, wherein the step of deriving the one or both of the impulse response and the transfer function comprises evaluating h(t) from $h(t)*[p_{x1}(t)-p_{x2}(t)*h_{m12}(t)]=[p_{x2}(t)*h_{m12}^{-1}(t)-p_{x1}(t)]$, where $h_{m12}(t)$ represents the transfer function between a first and second acoustic detection devices of the plurality of acoustic detection devices.

18. The system of claim 17, further comprising an excitation source for exciting the pipe using the excitation waveform via the launch body.

19. The system of claim 17, further comprising a sampler arranged to take a plurality of measurements via the acoustic detection devices; the plurality of measured resultant pressure waveforms being associated with the plurality of measurements.

20. The system of claim 17, further comprising a filter arranged to filter the plurality of measured resultant pressure waveforms prior to said resolving.

21. The system of claim 20, wherein the filter is arranged to apply one or more than one filter associated with a possible characteristic acoustic impedance.

22. The system claim 17, wherein the processor is arranged to resolve the plurality of measured resultant pressure waveforms into the number of associated waveforms comprises resolving the plurality of measured resultant pressure waveforms into a number associated linear waveforms representing differences between the measured resultant pressure waveforms.

23. The system of claim 22, wherein the differences between measured resultant pressure waveforms have an associated linear function or represent time shifted versions of the measured resultant pressure waveforms.

24. The system of claim 23, wherein the linear function or differences take the form $$f(p(t))=p(t+\tau)-p(t-\tau)$$

where
p(t) represents a measured resultant pressure waveform at time t; and
$\tau$ is associated with the separation between acoustic measuring devices.

25. The system of claim 17, wherein the processor is arranged to derive the one or both of the impulse response and the transfer function comprises evaluating h(t) from $h(t)*[p_{x1}(t)-p_{x2}(t-\tau)]=[p_{x2}(t-\tau)-p_{x1}(t)]$.

26. The system of claim 25, wherein the processor is arranged to derive the one or both of the impulse response and the transfer function comprises evaluating $$h(t) = IFFT\left\{\frac{FFT[p_{x2}(t+\tau) - p_{x1}(t)]}{FFT[p_{x1}(t) - p_{x2}(t-\tau)]}\right\}$$

where FFT represents a Fourier Domain Transform and IFFT represents an Inverse Fourier Domain Transform.

27. The system of claim 17, wherein the processor is arranged to derive the one or both of the impulse response and the transfer function comprises evaluating $$h(t) = IFFT\left[\frac{FFT[p_{x2}(t) * h_{m12}^{-1}(t) - p_{x1}(t)]}{FFT[p_{x1}(t) - p_{x2}(t) * h_{m12}(t)]}\right]$$

where FFT represents a Fourier Domain Transform and IFFT represents an Inverse Fourier Domain Transform, $h_{m12}(t)$ represents the transfer function between the acoustic detection devices at said respective positions and $h_{m12}^{-1}(t)$ is the inverse of $h_{m12}(t)$.

28. The system of claim 17, wherein the processor adapted to derive the one or both of the impulse response and the transfer function comprises evaluating h(t) from $h(t)*[p_{x2}^{+}(t+\tau)-p_{x2}^{+(t-\tau)}]=[p_{x2}^{-}(t+\tau)-p_{x2}^{-}(t-\tau0]$.

29. The system of claim 28, wherein processor adapted to derive the one or both of the impulse response and the transfer function comprises evaluating $$h(t) = IFFT\left\{\frac{FFT[p_{x2}^{-}(t+\tau) - p_{x2}^{-}(t-\tau)]}{FFT[p_{x2}^{+}(t+\tau) - p_{x2}^{+}(t-\tau)]}\right\}$$

where FFT represents a Fourier Domain Transform and IFFT represents an Inverse Fourier Domain Transform.

30. The system of claim 17, wherein processor adapted to derive the one or both of the impulse response and the transfer function is adapted to evaluate h(t) from $h(t)*[p_{x2}^+(t)*h_{m12}^{-1}(t)-p_{x2}^+(t)*h_{m12}(t)]=[p_{x2}^-(t)*h_{m12}^{-1}(t)-p_{x2}^-(t)*h_{m12}(t)]$.

31. The system of claim 30, wherein processor adapted to derive the one or both of the impulse response and the transfer function is adapted to evaluate $$h(t) = IFFT\left[\frac{FFT[p_{x2}^-(t)*h_{m12}^{-1}(t) - p_{x2}^-(t)*h_{m12}(t)]}{FFT[p_{x2}^+(t)*h_{m12}^{-1}(t) - p_{x2}^+(t)*h_{m12}(t)]}\right]$$

where FFT represents a Fourier Domain Transform and IFFT represents an Inverse Fourier Domain Transform, $h_{m12}(t)$ represents the transfer function between the acoustic detection devices at said respective positions and $h_{m12}^{-1}(t)$ is the inverse of $h_{m12}(t)$.

32. The system of claim 17, further comprising providing, or the processing being adapted to provide, an indication of the location within the pipe of the characteristic impedance.

33. Non-transitory machine readable storage storing machine-readable instructions arranged, when executed, to cause a computer system to resolve a plurality of measured resultant pressure waveforms, $p_{x1}(t)$, $p_{x2}(t)$, ..., $p_{xn}(t)$ and $p_{x2}(t)$, associated with the pipe into a number of associated waveforms; the number of associated waveforms being a function of the plurality of measured resultant pressure waveforms measured at respective positions; the plurality of measured resultant pressure waveforms representing measurements by a plurality of acoustic detection devices positioned at the respective positions of a launch body for exciting the pipe using an excitation waveform;

derive one or both of an impulse response, h(t), or of the pipe and a corresponding transfer function of the pipe from the number of associated waveforms; the one or both of the impulse response and the transfer function bearing the characteristic acoustic impedance associated with the pipe, wherein the step of deriving the one or both of the impulse response and the transfer function comprises evaluating h(t) from $h(t)*[p_{x1}(t)-p_{x2}(t)*h_{m12}(t)]=[p_{x2}(t)*h_{m12}^{-1}(t)-p_{x1}(t)]$, where $h_{m12}(t)$ represents the transfer function between a first and second acoustic detection devices of the plurality of acoustic detection devices.

* * * * *